(12) United States Patent
Edgerly-Plug

(10) Patent No.: US 6,596,305 B1
(45) Date of Patent: Jul. 22, 2003

(54) METHOD OF CONTROLLING THE SIZE OF LIPOSOMES

(75) Inventor: Laura M. Edgerly-Plug, Spotswood, NJ (US)

(73) Assignee: Elan Pharmaceuticals, Inc., South San Francisco, CA (US)

(*) Notice: Subject to any disclaimer, the term of this patent is extended or adjusted under 35 U.S.C. 154(b) by 0 days.

(21) Appl. No.: 08/442,077

(22) Filed: May 16, 1995

Related U.S. Application Data

(63) Continuation of application No. 08/088,742, filed on Jul. 8, 1993, now abandoned.

(51) Int. Cl.$^7$ ................................................. A61K 9/127
(52) U.S. Cl. ..................... 424/450; 428/402.2; 264/4.1; 264/4.3
(58) Field of Search ................................. 424/450, 1.21, 424/1.321, 9–51, 417, 94.3; 264/4.1, 4.3; 428/402.2

(56) References Cited

U.S. PATENT DOCUMENTS

| | | | | |
|---|---|---|---|---|
| 4,039,285 A | * | 8/1977 | Teipel ...................... 23/230 B |
| 4,184,849 A | * | 1/1980 | Cambiaso ................. 23/230 B |
| 4,522,803 A | | 6/1985 | Lenk et al. .................. 424/1.1 |
| 4,529,561 A | | 7/1985 | Hunt et al. ................... 264/4.3 |
| 4,588,578 A | | 5/1986 | Fountain et al. ............. 424/1.1 |
| 4,619,895 A | * | 10/1986 | Cubicciotti ..................... 435/7 |
| 4,687,551 A | | 8/1987 | Furneaux et al. ............. 204/11 |
| 4,721,612 A | | 1/1988 | Janoff et al. .................. 424/1.1 |
| 4,737,323 A | | 4/1988 | Martin et al. ................. 264/4.3 |
| 4,861,580 A | | 8/1989 | Janoff et al. .................. 424/1.1 |
| 4,897,384 A | | 1/1990 | Janoff et al. .................. 424/450 |
| 4,927,637 A | | 5/1990 | Morano et al. ............. 424/450 |
| 4,994,213 A | | 2/1991 | Aitcheson et al. ........... 264/4.6 |
| 5,000,887 A | * | 3/1991 | Tenzel et al. ................. 264/4.6 |
| 5,008,050 A | | 4/1991 | Cullis et al. .................. 264/4.3 |
| 5,077,056 A | | 12/1991 | Bally et al. .................. 424/450 |
| 5,082,664 A | | 1/1992 | Lenk et al. .................. 424/450 |
| 5,154,930 A | | 10/1992 | Popescu et al. ............. 424/489 |

FOREIGN PATENT DOCUMENTS

| | | | |
|---|---|---|---|
| EP | 0158441 | * 10/1985 | |
| WO | 89/00846 | 2/1989 | ............ A61K/9/00 |

OTHER PUBLICATIONS

Batzri, et al., "Single bilayer liposomes prepared without sonication", Biochem. Biophys Acta, 298:1015 (1973).

Munir Cheryan, *Ultrafiltration Handbook*, 205–213 and 377, Technomic Publishing Company (1986).

Szoka, "Procedure for preparation of liposomes with large internal aqueous space and high capture by reverse–phase evaporation", Proc. Natl. Acad. Sci, U.S.A, 75: 4194–8 (1978).

* cited by examiner

*Primary Examiner*—Gollamudi S. Kishore
(74) *Attorney, Agent, or Firm*—Burns, Doane, Swecker & Mathis, L.L.P.

(57) ABSTRACT

A process for producing liposomes having a desired mean particle size wherein the desired mean particle size is obtained by varying the initial organic solvent concentration.

8 Claims, No Drawings

METHOD OF CONTROLLING THE SIZE OF LIPOSOMES

This is a continuation of application Ser. No. 08/088,742 filed on Jul. 8, 1993 now abandoned.

FIELD OF THE INVENTION

The present invention is generally directed to a method of producing liposomes and particularly to a method in which the particle size of the liposome population is controlled by the amount of organic solvent.

BACKGROUND OF THE INVENTION

Methods of forming liposome vesicles for the association of a bioactive agent are well known. As used herein the term "association" shall mean bioactive agent which is encapsulated within the liposome and bioactive agent which, while not encapsulated, remains with the liposome and is not readily separated therefrom.

Some methods of forming liposomes employ an organic solvent to dissolve a lipid alone or the lipid and a bioactive agent such as a drug. For example, in Bally et al., U.S. Pat. No. 5,077,056, lipids are dissolved in an organic solvent and combined with an aqueous medium to form liposomes. Then a bioactive agent such as a drug is loaded into the preformed liposomes using a transmembrane concentration gradient. On the other hand, in Lenk et al., U.S. Pat. No. 5,082,664, a lipid and a bioactive agent are dissolved together in an organic solvent, and combined with an aqueous medium to form liposomes associated with the bioactive agent. In particular, the lipid and the bioactive agent (e.g. lipophilic drugs such as the prostaglandins) are co-dissolved in an aqueous-miscible organic solvent such as ethanol, then added slowly to an aqueous solution, which may additionally contain a drying protectant and/or a buffer, as discussed in the Lenk et al. patent. Both of these patents are hereby incorporated by reference into the present disclosure.

Another method for forming liposomes employs ethanol injection and is discussed in Batzri et al., *Biochem. Biophys. Acta*. 298:1015 (1973). The ethanol injection method has been used to form liposomes having associated therewith a lipophilic or hydrophilic bioactive agent. When forming liposomes containing a lipophilic bioactive agent (e.g. prostaglandin), an optional preservative and the bioactive agent are added to the ethanol containing lipid. The resulting mixture is then slowly added to an aqueous medium. This process forms liposomes entrapping the aqueous medium. Ethanol injection processes, as well as other liposome formation processes, using a desalted charged lipid are disclosed in Popescu et al., U.S. Pat. No. 5,154,930, incorporated by reference into the present specification. A method of controlling size distribution of resultant liposomes in an ethanol infusion process is discussed in Aitcheson et al., U.S. Pat. No. 4,994,213.

For the formation of liposomes having a hydrophilic bioactive agent associated therewith (e.g. aminoglycoside antibiotics, such as gentamicin), the bioactive agent is added to the aqueous phase. The lipid and ethanol are combined to form a solution which is added to the aqueous phase and the resulting mixture is processed to form liposomes. The aqueous phase may be a solution of one or more drying protectants with or without a preservative.

The liposome preparations prepared by such methods typically contain liposomes having a wide variety of particle sizes. It is often desirable to reduce the size of the larger liposomes to obtain a single-modal population distribution encompassing a desired mean particle size. The term "single-modal population distribution" as used herein shall mean that most of the liposomes have a particle size within a continuous range of particle sizes encompassing the mean particle size. The term "mean particle size" shall mean the sum of the diameters of each liposome of the population divided by the total number of liposomes.

Size reduction to obtain a single-modal population distribution can be achieved by a number of methods such as by extrusion through a filter, as described in Pieter Cullis et al., U.S. Pat. No. 5,008,050, incorporated herein by reference.

A method of sizing liposomes by filtration through a 200 nm Unipore™ polycarbonate filter is discussed in Szoka, *Proc. Natl. Acad. Sci. U.S.A.* 75:4194–8 (1978). A size-processing method based on liposome extrusion through a series of uniform straight-pore type polycarbonate membranes is described in Hunt et al., U.S. Pat. No. 4,529,561.

U.S. Pat. No. 4,737,323, describes a method for sizing liposomes by extrusion through an asymmetric ceramic filter. Such filters are designed for operation at relatively high pressure, and can be backflushed to prevent clogging. U.S. Pat. No. 4,927,637, describes a method of sizing liposomes by passing them through a polymer filter having a web-like "tortuous-path" construction.

An alternative type of filter medium is described in Furneaux et al., U.S. Pat. No. 4,687,551. This patent discloses a filter sheet comprising an anodic aluminum oxide film having branched pores extending from one surface of the film to the other. The film is unique in that it includes a system of larger pores extending in from one face and a system of smaller pores extending in from the other face. The system of larger pores interconnects with the system of smaller pores such that the inner ends of one or more smaller pores are joined to the inner end of a larger pore and there are substantially no larger pores that terminate within the film.

The application of an aluminum oxide porous film to the size reduction of liposomes is disclosed in Royden M. Coe et al., U.S. Ser. No. 771,267 filed on Oct. 4, 1991.

Homogenization is another method for size reducing liposomes. In a simple homogenization method, a suspension of liposomes is repeatedly pumped under high pressure through a small orifice or reaction chamber until a desired size distribution is achieved.

The size reduction procedures described above for controlling the size of the final liposome product are time consuming and add significantly to the cost of producing liposomes. It would, therefore, be a significant advance in the art to provide a process for preparing liposomes in which the initial liposome preparation has a population of liposomes with a more uniform size distribution than that obtained with conventional liposome forming methods. As a consequence, the costly and time consuming post-production sizing procedures can be reduced or even eliminated.

It would be a further advance in the art to provide a process of making liposomes that can result in a single-modal population distribution of liposomes encompassing a preselected desired mean particle size.

SUMMARY OF THE INVENTION

The present invention is generally directed to a process of making liposomes by dissolving a lipid in an organic solvent. The concentration of the organic solvent is selected in accordance with a desired mean particle size. The resulting liposome population has a more uniform particle size distribution than prior processes where the concentration of organic solvent is not selected as required in the present invention.

In accordance with the present invention, there is provided a process for producing a population of liposomes having a desired mean particle size, the process comprising forming a mixture of vesicle-forming lipids in a single-phase solvent system containing a water-miscible organic solvent and water, the improvement comprising controlling the mean particle size of the population of liposomes by adjusting the initial concentration of solvent in said solvent system.

The present process can reduce or eliminate the need for costly and time consuming size reduction procedures to obtain a single-modal population distribution of liposomes encompassing a desired mean particle size. In accordance with one aspect of the invention, a desired mean particle size is chosen and the concentration of organic solvent selected which will produce a single-modal population distribution of liposomes encompassing the desired mean particle size, without having to rely on extensive post-production filtering procedures. I In a particular embodiment of the present invention the step of adjusting the initial concentration of solvent comprises:

(a) forming a first test sample of a population of liposomes from a solvent system having a preselected initial concentration of solvent;

(b) forming a second test sample from a solvent system having a different preselected initial concentration of solvent;

(c) determining the mean particle sizes of the liposomes in said first and second test samples;

(d) adjusting the initial concentration of solvent to be used in subsequent processes based on which determined mean particle size is closer to the desired mean particle size; and (e) repeating steps (a) through (d) until a concentration of solvent is found which yields a population of liposomes with a mean particle size acceptably close to the desired mean particle size.

DETAILED DESCRIPTION OF THE INVENTION

The present invention is premised in part on the discovery that within a range of the ratio of the weight of lipid to the volume of organic solvent employed, the particle size of the liposomes will vary inversely within a first concentration range of the organic solvent and directly within a second concentration range of the organic solvent, wherein the concentrations in the second range are greater than the concentrations in the first range. The upper limit of the ratio is that point at which the lipid will no longer dissolve in the organic solvent. The lower limit is that point at which liposomes will no longer form because of the presence of excessive solvent.

The concentration of the organic solvent employed in the present invention correlates to the particle size of the resulting liposomes and, therefore, provides a simple method of obtaining a population distribution of liposomes encompassing a desired mean particle size, preferably a single-modal population distribution of liposomes. It has been found in general within a range of lipid to organic solvent ratios, as the concentration of the organic solvent added to the reaction mixture increases, the mean particle size of the liposome population decreases in a first concentration range, thereafter the mean particle size of the liposomes will increase in a second concentration range, greater than the first concentration range, at which point the liposomes will no longer be able to form because of the presence of excessive solvent. The minimum mean particle size will occur at approximately the junction of the first and second concentration ranges.

The present invention provides a relatively simple way of obtaining a population distribution of liposomes, preferably a single-modal population distribution of liposomes encompassing a desired mean particle size without the need for size reducing procedures requiring numerous passes through sizing filters as mentioned above in connection with prior art processes.

A particular type of lipid material for use in this invention is one which is amphipathic in character. Hydrophilic character can be imparted to the molecule through the presence of phosphato, carboxylic, sulphato, amino, sulfhydryl, nitro, and other like groups. Hydrophobicity can be conferred by the inclusion of groups that include, but are not limited to, long chain saturated and unsaturated aliphatic hydrocarbon groups and such groups substituted by one or more aromatic, cycloaliphatic or heterocyclic group. The preferred amphipathic compounds are phosphoglycerides, representative examples of which include phosphatidylcholine, phosphatidylethanolamine, lysophosphatidylcholine, lysophosphatidylethanolamine, phosphatidylserine, phosphatidylinositol, phosphatidic acid, dimyristoylphosphatidylglycerol and diphosphatidylglycerol alone or in combination with other lipids. Synthetic saturated compounds such as dimyristoylphosphatidylcholine, dipalmitoylphosphatidylcholine, or distearoylphosphatidylcholine or unsaturated species such as dioleoylphosphatidylcholine or dilinoleoylphosphatidylcholine might also be usable. Other compounds lacking phosphorus, such as members of the sphingolipid and glycosphingolipid families, are also within the group designated as lipid.

A variety of cholesterols and other sterols and their water soluble derivatives have also been used to form liposomes; see specifically Janoff et al., U.S. Pat. No. 4,721,612 and references referred to therein, all of which are incorporated herein by reference. Various tocopherols and their water soluble derivatives have also been used to form liposomes, as disclosed in Janoff et al. U.S. Pat. No. 4,861,580, incorporated herein by reference. Preferred of this group are cholesterol hemisuccinate and tocopherol hemisuccinate.

Water miscible organic solvents are employed in the present invention. Such solvents include lower alkanols, such as methanol, ethanol, propanol, butanol, isoamyl alcohol, isopropanol, 2-methoxy ethanol, acetone and the like. Ethanol is particularly preferred.

The liposomes of the present invention may be formulated with a bioactive agent. The bioactive agents, which may be associated with the liposomes prepared in accordance with the present invention, include nucleic acids, polynucleotides, antibacterial compounds, antiviral compounds, antifungal compounds, antiparasitic compounds, tumoricidal compounds, proteins, toxins, enzymes, hormones, neurotransmitters, glycoproteins, immunoglobulins, immunomodulators, dyes, radio labels, radio-opaque compounds, fluorescent compounds, polysaccharides, cell receptor binding molecules, anti-inflammatories, antiglaucomic agents, mydriatic compounds, local anesthetics, and the like. Specific examples of such active agents and their incorporation into liposomes can be found in Lenk et al., U.S. Pat. No. 4,522,803; Fountain et al., U.S. Pat. No. 4,588,578; Janoff et al., U.S. Pat. Nos. 4,861,580 and 4,897,384; and Lenk et al., U.S. Pat. No. 5,082,664; each of which is incorporated herein by reference.

The bioactive agents which find particularly effective application to the present invention are lipophilic bioactive agents, particularly arachidonic acid metabolites including their structural analogs and synthetic enzyme inhibitors. One class of such arachidonic acid metabolites is the group of bioactive agents known as prostaglandins including, but not limited to prostaglandin $E_1$.

Hydrophilic bioactive agents, such as the aminoglycoside antibiotics and their structural analogs, are examples of hydrophilic bioactive agents. These include gentamicin, streptomycin, dihydrostreptomycin, tobramycin, neomycin B, paromycin, ribostamycin, lividomycin, kanamycin, viomycin, sisomicin, netilmicin and amikacin, as well as analogues and derivatives thereof. Gentamicin is the preferred aminoglycoside antibiotic.

The process of forming liposomes, in accordance with the present invention depends in part on whether a lipophilic or hydrophilic bioactive agent is to be associated with the liposomes. For lipophilic associated liposomes, an optional preservative such as BHT and the bioactive agent (e.g. prostaglandin $E_1$) are dissolved in the organic solvent and the solution is then added to an aqueous medium, which may contain a buffer (e.g. citrate or phosphate) and/or a drying protectant such as maltose.

If a hydrophilic bioactive agent such as gentamicin is to be associated with the liposomes, then the gentamicin is added to the aqueous phase (which may contain a buffer, a drying protectant, and/or a preservative such as disodium EDTA) to form a solution. The lipid dissolved in the organic solvent is added to the aqueous solution. The resulting mixtures containing either the lipophilic or hydrophilic bioactive agent are processed in a conventional manner by vigorous mixing until a liposome population is formed. Alternatively, the liposomes may be prepared by adding the bioactive agent after the liposomes have formed.

The bulk liposomes produced by the process of the present invention may be separated from unassociated bioactive agent, if necessary, as well as from free lipid, salts and water by the common technique of ultrafiltration such as disclosed in Munir Cheryan, *Ultrafiltration Handbook*, pp. 205–213 and 377, Technomic Publishing Company (1986).

Diafiltration is one such ultrafiltration system in which permeable solutes are removed by the addition of fresh solvent or other solution to the feed liquid. The remaining liquid (the retentate) containing non-permeated substances containing the desired liposome product is recovered. A preferred method of diafiltration is disclosed in Lenk, et al., PCT Published Application No. WO89/00846, the disclosure of which is incorporated herein by reference.

Diafiltration systems typically employ a filter having one or more primary pathways formed by a porous filter composition. The filter device has a rated pore size such that generally materials having a size equal to or less than the rated pore size will be able to pass through the filter device via narrower secondary pathways. Generally, the larger components will remain in the primary pathways and pass through the filter device as part of the liquid retentate. When liposomes are prepared using a diafiltration system, the liposomes pass out of the filter device through the primary pathways while the permeable solutes pass through the narrower secondary pathways.

The process of the present invention is generally carried out by selecting a desired mean particle size for the type of liposomes which are to be produced. For example, a 150 to 200 nm mean particle size for gentamicin associated liposomes is desirable. A test batch of liposomes is then prepared using a fixed amount of lipid and a fixed concentration of the organic solvent.

The maximum ratio of lipid to organic solvent that may be selected must be sufficient to produce liposomes, i.e. if too much solvent is present liposomes will not form. The minimum ratio is determined by the point at which the lipid will no longer dissolve in the solvent. The ratio of the fixed amount of lipid to organic solvent must fall within the minimum to maximum ratios.

The mean particle size of the test batch is then determined in a conventional manner such as by measurement with a submicron particle sizer (e.g. NICOMP Model 270 Submicron Particle Sizer). If the mean particle size of the test batch corresponds to the desired mean particle size, then the process is conducted using the same ratio of lipid to organic solvent (i.e. keeping the same concentration of the organic solvent) employed for the test batch. If, however, the mean particle size of the test batch does not correspond to the desired mean particle size, then the ratios of lipid to organic solvent must change, such as by changing the organic solvent concentration. The change in concentration of the organic solvent is dependent on the initial concentration of the organic solvent and the difference between the mean particle size of the test batch and the desired mean particle size.

EXAMPLE 1

4.4 mg of egg phosphatidylcholine (EPC), 0.03 mg of butylated hydroxytoluene (BHT) and 5.58 mL of ethanol were combined and mixed until a homogenous mixture was formed. 100 g of maltose was mixed with 900 mL of water for injection (WFI), sterilized by filtration, and added to a 3 liter jacketed glass reactor equipped with one 3 inch R-100 impeller and the reactor was maintained at ambient temperature. The impeller was activated at 2,000 RPM at which time the EPC/BHT/ethanol solution was added to the maltose solution contained within the reactor. The impeller was maintained at 2,000 RPM for a total of 15 minutes. Upon completion of the mixing, the contents of the reactor were brought to a final volume of one liter with water for injection.

The particle size of the resulting liposomes was measured using a NICOMP Model 270 Submicron Particle Sizer and was found to be greater than 1,200 nm, which is the measuring limit of the particle size measuring device employed.

EXAMPLES 2–4

The procedure set forth in Example 1 was repeated using initial ethanol concentrations of 5.0%, 10.0% and 15.0% by volume, respectively, based on the total volume contained in the reactor. The results are shown in Table 1.

TABLE 1

| EXAMPLE | AMOUNT ETHANOL % OF TOTAL BATCH | MEAN PARTICLE SIZE |
|---|---|---|
| 1 | 0.558% | >1,200 nm |
| 2 | 5.0% | 266 nm |

TABLE 1-continued

| EXAMPLE | AMOUNT ETHANOL % OF TOTAL BATCH | MEAN PARTICLE SIZE |
|---|---|---|
| 3 | 10.0% | 183 nm |
| 4 | 15.0% | 238 nm |

The process of the present invention will now be explained with reference to the data shown and described in connection with the Examples.

It has been found that for the formation of-liposomes using egg phosphatidylcholine as the lipid and ethanol as the solvent, there is a substantial continuous decrease in the mean particle size of the resulting liposomes as the concentration of the organic solvent increases from about 0.558% to 10.0% by volume (i.e. the first concentration range) while the amount of lipid remains fixed (4.4 mg). As the concentration of the organic solvent increases from about 10.0% to 15.0% by volume (the second concentration range), the mean particle size of the thus formed liposomes increases.

Beyond about a 15.0% concentration of ethanol, the lipid will not form liposomes, but instead will remain dissolved in the ethanol. In accordance with this example, the lipid/solvent ratio is at least 0.03 mg/mL, preferably 0.03 to 0.80 mg/mL. Within this range, the particle size of the liposomes will decrease in the first ethanol concentration range of about 0.558% to 10.0% by volume ethanol as shown by Examples 1–3 and increase in the second ethanol concentration range of about 10.0% to 15.0% by volume as shown by Examples 3 and 4.

The process is commenced by preselecting a desired mean particle size. For example, a mean particle size of about 100 to 200 nm, preferably in the range of about 150 to 190 nm is desired for a number of liposome products.

A test batch of the liposome formulation containing EPC and ethanol is then prepared according to the method of Example 1. If 200 nm is preselected as the desired mean particle size, then the test batch can be prepared at, for example, about an 8% by volume ethanol concentration or about an 11% by volume ethanol concentration. It is generally preferred to initially operate within the first ethanol concentration range (i.e. 0.558 to 10% by volume) in order to keep the amount of solvent as low as possible to reduce cost and minimize disposal problems. Thus, an 8% ethanol concentration is chosen.

The mean particle size of the liposomes in the test batch is determined as described in Example 1. If the desired mean particle size is less than the mean particle size for the test batch, then a higher ethanol concentration should be selected. Conversely, if the desired mean particle size is greater than the mean particle size for the test batch, then a lower ethanol concentration should be chosen.

If an 11% by volume concentration of ethanol is chosen and the desired mean particle size is lower than the test batch mean particle size, then the ethanol concentration should be reduced, but not to a concentration of less than 10% by volume. Conversely, if the desired mean particle size is greater than the test batch mean particle size, the ethanol concentration is increased, but no greater than about 15.0% by volume.

If sufficient similarity to the desired mean particle size cannot be obtained within one of the two concentration ranges (e.g. the first concentration range), then a test batch should be prepared using an ethanol concentration within the other of the concentration ranges (e.g. the second concentration range). In addition, it may be desirable to run more than one test batch if a more accurate correlation with the desired mean particle size is needed for a particular application.

In accordance with the present invention, the formation of a liposome population having a mean particle size corresponding to a desired mean particle size can be achieved for a variety of lipids and water-miscible organic solvents. The operable range of the lipid to organic solvent ratio for the selected lipid and organic solvent can be routinely determined and the process conducted in accordance with the methods described herein. The addition of either a lipophilic or hydrophilic bioactive agent will not materially change the process which can be used to form liposome populations containing highly potent therapeutic agents for use in treating warm-blooded animals including humans.

What is claimed is:

1. A method for producing a pharmaceutical composition comprising a liposome population having a predetermined mean particle size comprising combination of a water-miscible organic solvent and a lipid according to the steps of:

(a) preparing a first solution comprising the lipid, the solvent and an aqueous phase and then removing the solvent so as to form liposomes, wherein the concentration of the solvent is from about 0.5% to less than about 10% by volume of the solution;

(b) preparing a second solution comprising the lipid, the solvent and an aqueous phase and then removing the solvent so as to form liposomes, wherein the concentration of the solvent is about 10% by volume of the solution;

(c) preparing a third solution comprising the lipid, the solvent and an aqueous phase and then removing the solvent so as to form liposomes, wherein the concentration of the solvent is from about 10 to 15% by volume of the solution;

(d) determining the mean particle sizes of liposomes prepared in accordance with steps (a), (b) and (c);

(e) comparing the mean particle sizes with the solvent concentration used;

(f) selecting an organic solvent concentration corresponding to a desired mean particle size; and (g) preparing a solution comprising the lipid, solvent and an aqueous phase, wherein the organic solvent concentration is selected according to step (f), wherein the lipid comprises egg phosphatidylcholine and the solvent concentration in a solution is at most about 15%.

2. The method of claim 1, wherein the solvent is a lower alkanol selected from the group consisting of methanol, ethanol, 2-methoxy ethanol, propanol, isopropanol and butanol.

3. The method of claim 2, wherein the solvent is ethanol.

4. The method of claim 1, wherein the organic solvent concentration of step (a) is about 5% by volume of the solution and the organic solvent concentration of step (b) is about 15% by volume of the solution.

5. The method of claim 1, further comprising repeating step (a) one or more additional times and determining the mean particle size of the resulting liposomes in accordance with step (d).

6. The method of claim 1, further comprising repeating step (c) one or more additional times and determining the mean particle size of the resulting liposomes in accordance with step (d).

7. A population of liposomes having a predetermined mean particle size produced in accordance with the method of claim 1.

8. The liposome population of claim 7, wherein the liposomes comprise a bioactive agent.

* * * * *